United States Patent [19]

Carlsson et al.

[11] 4,080,471

[45] Mar. 21, 1978

[54] USE OF SUBSTITUTED ISOPROPYLAMINOPROPANOLS FOR INDUCING INOTROPIC EFFECTS OF THE HUMAN HEART

[75] Inventors: Enar Ingemar Carlsson, Kungsbacka; Nils Henry Alfons Persson, Dalby; Gustav Benny Roger Samuelsson, Molnlycke; Kjell Ingvar Leopold Wetterlin, Sandby, all of SW

[73] Assignee: Aktiebolaget Hassle, Gothenburg, Sweden

[21] Appl. No.: 699,627

[22] Filed: Jun. 25, 1976

[51] Int. Cl.$^2$ .................. A61K 31/235; A61K 31/22; A61K 31/135

[52] U.S. Cl. .................... 424/308; 424/311; 424/330

[58] Field of Search .......... 424/330, 308, 311

[56] References Cited

U.S. PATENT DOCUMENTS

| | | | |
|---|---|---|---|
| 3,501,769 | 3/1970 | Crowther et al. | 260/501.17 |
| 3,740,443 | 6/1973 | Koppe et al. | 424/330 |
| 3,857,891 | 12/1974 | Holmes et al. | 260/570.7 |

FOREIGN PATENT DOCUMENTS 1,069,345  5/1967  United Kingdom ............ 260/501.17

OTHER PUBLICATIONS

Chemical Abstracts, vol. 72, 1970, pp. 355-356, (111007).

Primary Examiner—Albert T. Meyers
Assistant Examiner—Daren M. Stephens

Attorney, Agent, or Firm—Brumbaugh, Graves, Donohue & Raymond

[57] ABSTRACT

A method for inducing increased inotropic effects of the human heart without inducing arrhythmogenic effects, but providing an antiarrhythmogenic effect therein. The method is effected by administering to mammals, including man, a compound of the formula

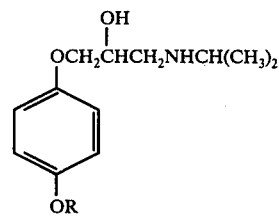

wherein R is selected from the group consisting of hydrogen or

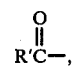

wherein R' is selected from the group consisting of straight or branched aliphatic alkyl having 1 to 7 carbon atoms, phenyl, benzyl, and phenylethyl, wherein the phenyl nucleus may be further substituted with alkyl having 1 to 4 carbon atoms, alkoxy having 1 to 4 carbon atoms, alkoxyalkyl having 2 to 8 carbon atoms or halogen, in any position.

5 Claims, No Drawings

USE OF SUBSTITUTED ISOPROPYLAMINOPROPANOLS FOR INDUCING INOTROPIC EFFECTS OF THE HUMAN HEART

The present invention relates to a method for inducing increased contractility of the human heart with little effect on rate and without arrhythmogenic effects therein by administering to humans certain substituted isopropylaminopropanols.

The compounds used are those of the general formula

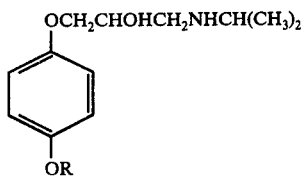

wherein R is selected from the group consisting of hydrogen or

wherein R' is selected from the group consisting of straight or branched aliphatic alkyl having 1 to 7 carbon atoms, phenyl, benzyl, and phenylethyl, wherein the phenyl nucleus may be further substituted with alkyl having 1 to 4 carbon atoms, alkoxy having 1 to 4 carbon atoms, alkoxyalkyl having 2 to 8 carbon atoms or halogen, in any position.

The compound of the formula above wherein R is hydrogen is previously described in U.S. Pat. Ser. No. 3,501,769 of Crowther et al to ICI Ltd. England, having a β-receptor blocking activity and is said to be useful in the treatment of coronary artery disease, i.e. in a disease where the oxygen demand of the heart are to be reduced by blocking cardiac beta-receptors controling beat frequency and contractility.

Many heart diseases create such extensive damage to the muscle of the myocardium that a heart insufficiency occurs.

A fundamental component in the therapy of heart insufficiency is an agent which has a positively inotropic action on the heart, i.e. one which increases the contractile force of the heart. Presently, the most commonly used agents are the glycosides of digitalis. However, the digitals preparations show evident drawbacks from a therapeutic point of view. They have a low therapeutic range. For example, they cause arrhythmogenetic effects in the heart when dosages insignificantly exceed those dosages which have a positively inotropic effect. Thus, there is an evident therapeutic need of positively acting inotropic, agents, which can replace or complement the digitalis preparations. The substances of this invention constitute such agents according to the results obtained in animal experiments. The positively acting inotropic effect of these substances depends on the activation of the adrenergic receptors which control the contractility of the heart. They have the feature of increasing the contractile force of the heart in dosages which have no or very little effect on other functions controlled by the adrenergic receptors, for example, heart frequency or peripheral vascular resistance. They differ in these respects from other known adrenergic agonists.

Four substances according to this invention are described below, namely (I) 1-isopropylamino-3-(p-hydroxyphenoxy)-propanol-2, (II) 1-isopropylamino-3-(p-isobutyryloxyphenoxy)-propanol-2, (III) 1-isopropylamino-3-(p-benzoyloxyphenoxy)-propanol-2, and (IV) 1-isopropylamino-3-(p-pivaloyloxyphenoxy)-propanol-2.

Compounds II, III and IV are the esters of compound I with isobutyric acid, benzoic acid and pivalic acid, respectively.

Salt forming acids may be used in preparing therapeutically acceptable salts of the esters, these are: hydrohalogen acids, sulfuric acid, phosphoric acid, nitric acid, perchloric acid, aliphatic, alicyclic, aromatic or heterocyclic carboxy or sulfonic acids, such as formic, acetic, propionic, succinic, glycolic, lactic, malic, tartaric, citric, ascorbic, maleic, hydroxymaleic, or pyruvic acid, phenylacetic, benzoic, p-aminobenzoic, anthranilic, p-hydroxybenzoic, salicyclic or p-aminosalicyclic acid, embonic acid, methanesulfonic, ethanesulfonic, hydroxyethane sulfonic, ethylenesulfonic, halogenbenzenesulfonic, toluenesulfonic, napthylsulfonic, or sulfanilic acid, methionine, tryptophane, lysine or arginine.

The substances are intended to be administered orally or parenterally for acute and chronic treatment of cardiac failure, specifically, ventricular myocardial failure (disease conditions with a diminution in ventricular contractility below that of a normal heart such that the capacity of the myocardium, at any given fiber length, to develop tension or to shorten against a load is so impaired as to compromise the circulation). Accordingly, the substances are intended to improve symptons and signs of cardiac failure such as dyspnea, cyanosis, pulmonary edema, increased venous pressure, liver enlargement, and peripheral edema.

The substances may be used alone and in combination with other therapeutic measures, such as administration of digitalis and diuretic drugs. Also, the substances may be used in combination with other measures in treating cardiogenic shock, the condition associated with reduced arterial blood pressure which often complicates myocardial infarction. Another use for the substances is in treatment of bradycardia, that is, conditions with slow heart rhythm where the weak positive chronotropic effect in combination with the positive inotropic effect of the substances can be expected to be of therapeutic value.

The biological effects of the 1-isopropylamino-3--(p-hydroxyphenoxy)-propanol-2 and its related esters have been tested, and the different tests carried out will be shown and explained bleow.

EXAMPLE A

Beta-adrenergic Effects of Isoprenaline, 1-isopropylamino-3-(p-hydroxyphenoxy)-propanol-2 and Its Related Esters On An Anesthetized Cat Pretreated With Reserpine Chronotropic (heart frequency) and vasodilatating effects:

Cats having an average weight of 3 kg were treated with reserpine (5 mg/kg bodyweight intramuscularily) about 16 hours before the test. This treatment eliminated completely the reflex sympathetic control of the heart and the vascular tonus. When the cats had been anaesthetized with Mebumal ® 30 mg/kg bodyweight i.p., an artificial air respiration was started. The two vagus nerves were cut and the blood passing through a femoral artery was fed via a catheter and a pump back to the distal part of the vessel. Parallelly, a pressure transducer was connected by which the perfusion pressure was registered. At a perfusion with a constant flow, the perfusion pressure is directly proportional to the peripheral resistance of the vascular bed of the hind limb. Blood circulation in the foot was interrupted with a ligature. Heart frequency was registered with a cardiotachometer triggered by the ECG. The substances were administered intravenously in increasing doses and the dose-response curves of the heart frequency and the vasodilatation were constructed.

In Table I below, the $ED_{50}$ values are given, i.e., the estimated doses which give 50% of maximal effect. Further, the dose ratios ($ED_{50}$ for vasodilatation/$ED_{50}$ for heart frequency) are calculated. A dose ratio $>1$ indicates a heart selective effect.

Table I

| Compound | Affinity $ED_{50} \mu g/kg$ | | Selectivity |
|---|---|---|---|
| | Heart Frequency | Vasodilation | $\dfrac{ED_{50} \text{ Vasodilatation}}{ED_{50} \text{ Heart Frequency}}$ |
| Isoprenaline | 0.05 | 0.01 | 0.2 |
| I | 6 | >1000 | >100 |
| II | 6 | >1000 | >100 |
| III | 10 | >1000 | >100 |
| IV | 60 | >1000 | > 15 |

Compounds I, II and III are about 1/100 as potent as isoprenaline as regards the chronotropic effect but less than 1/100,000 as potent as isoprenaline as regards the vasodilating effect. The maximal heart frequency response for compounds I-IV was about 80% of a maximum isoprenaline response. In two separate tests, compound I was administered (0.01 mg/kg bodyweight i.v.) before and after an intravenous injection of 0.2 mg/kg bodyweight of 1-isopropylamino-3- (1-naphthoxy)-propanol-2, which is an adrenergic beta-blocking compound sold by ICI under the name Inderal ®. When compound I was administered before Inderal ®, said dose increased the heart frequency by 60 beats/minute as an average. When administered after Inderal ®, the heart frequency was only increased by 10 beats/minute.

The above results indicate that compounds I-IV are highly heart selective, beta-stimulating substances.

EXAMPLE B

Chronotropic (Heart Frequency) and Inotropic (Contractile Force) Effects

The following parameters were registered on a reserpinized, anesthetized and vagotomized cat, namely: heart frequency, mean blood pressure in the carotis artery, intraventricular pressure in the left ventricle (P), the first derivative of P (dP/dt) and the pressure in left auricle. The mean blood pressure was regulated with an adjustable clamp around the descending aorta. All registrations were than able to be done at a constant pressure in aorta (afterload). The compounds were administered by infusion intravenously in increasing doses. The dose-response curves as regards the heart frequency and maximum dP/dt were constructed, from which the $ED_{50}$-values were estimated.

Maximum dP/dt is a measure of the contractile force of the heart, i.e. inotropy, but is influenced by changes in the heart frequency, filling pressure (preload) and aortic blood pressure (afterload). In this test, a comparison between inotropic and chronotropic effects can be done at the same heart frequency. Further, the aortic blood pressure is kept constant. The auricle pressure (filling pressure) showed small changes. The tendency, however, was that it decreased after the administration of compound I. This means that the inotropic effects of compound I was slightly underestimated. At a 50% heart frequency effect, the inotropic effect of isoprenaline was about 30%, while the inotropic effect of compound I was 70 to 80%.

The test results indicate that compound I has a higher affinity to cardiac beta-receptors, which give inotropic effects, than to beta-receptors in the sinus-node region, which give chronotropic effects.

EXAMPLE C

The Effect of Compounds I and II and Isoprenaline and Ouabain On The Heart Chronotropy and Inotropy of A Conscious Dog During anesthesia a catheter was introduced in the aorta, an electromagnetic flow probe was placed around the ascending aorta, and induction coils were placed diametrically on the inside of the left ventricle. The experiments were started about 2 weeks after the incision, when the dog had recovered completely.

When the dog was resting, the arterial blood pressure, the flow in the aorta, the maximum flow acceleration in the aorta (maximum dF/dt), heart frequency, the diameter of the left ventricle, and ECG were registered. The effects of compounds I and II were registered at 10, 20, and 30 minutes after administration. Isoprenaline was administered by infusion and the registration took place at steady state. The effects of ouabain were registered at maximum response which occurred about 50 minutes after administration. The compounds were given intravenously in the following doses. Compounds I and II; 10 and 20 μg/kg bodyweight, respectively, isoprenaline 10 and 20 μg/kg bodyweight and ouabain 30 μg/kg bodyweight. In order to eliminate vagal influence on the heart the dog was pretreated with methyl scopolamine 0.012 mg/kg bodyweight intramuscularily 20 minutes before the administration of the compounds. From the data giving the diameter of the left ventricle, the end diastolic volume was calculated according to E. W. Hawthorne. Mean ejection rate (ml/sec.) was calculated by dividing the stroke volume with the ejection time. In Table 2 the results obtained are shown. The values given are the percentage changes after administration when the heart frequency has increased 10 beats per minute, values interpolated. After the administration of ouabain an expected decrease of the heart frequency was obtained. In order to compare the inotropic effects of ouabain with those of the other compounds, the heart was stimulated in these experiments by electric pacing to a frequency which was 10 beats/minute above that registered before administration.

It is evident from the table that compound I compared with the control increases the contractility of the left ventricle registered as a certain increase of the stroke volume at a decreased preload (a decreased end-diastolic volume) and an unchanged afterload (unchanged pressure in the aorta), and a simultaneous increase of maximum dF/dt, mean ejection rate, and peak aortic flow.

Isoprenaline decreased the mean blood pressure depending on a decreased peripheral vascular resistance. This decrease of afterload may to some extent explain the increase of stroke volume, maximum dF/dt, mean ejection rate, and peak aortic flow. It is then probable that isoprenaline increased the contractility less than compounds I and II (at the same chronotropic effect) also in this series.

The positive inotropic effect of compounds I and II were comparable to the effect of the relatively high dose of ouabain, which caused vomiting. No side effect was observed after the administration of compounds I and II.

In order to investigate the absorption and duration of the effect, compounds I and II were given orally in an amount of 100 μg/kg bodyweight. Maximum effect was obtained 30 minutes after administration and the effects were comparable with those obtained after intravenous administration of 20 μg/kg bodyweight. The effect lasted for 3 to 4 hours.

Ouabain was given in 3 consecutive doses of 20 μg/kg bodyweight. In the combination test ouabain was first given in a dose of 20 μg/kg bodyweight followed by two doses of compound I of 10 and 20 μg/kg bodyweight, respectively.

Ouabain increased maximum dP/dt. The effect started within a minute, became maximal after about 20 minutes and was only partly reduced after 50 minutes. Even compound I increased the maximum dP/dt. The effect being immediate, and reached its maximum after 5 to 10 minutes, and was almost completely reduced after 50 minutes.

In the following, the effects 20 minutes after administration are discussed. A dose of 20 μg/kg bodyweight of ouabain increased maximum dP/dt approximately to the same level as a dose of 10 μg/kg bodyweight of compound I. The effect of 40 μg/kg bodyweight of Table 2

| Substance | Heart rate frequency beats/min | Stroke volume percent | Enddiastolic volume percent | Max. dF/dt percent | Mean ejection rate percent | Peak aortic flow percent | Mean arterial blood pressure mm Hg |
|---|---|---|---|---|---|---|---|
| I | 10 | 5 | −9 | 43 | 13 | 22 | 0 |
| II | 10 | 5 | −8 | 34 | 11 | 19 | 0 |
| Isoprenaline | 10 | 10 | −2 | 18 | 10 | 19 | −10 |
| Ouabain (30 μg/kg i.v.) | 10* (paced) | 5 | −2 | 30 | 10 | 12 | 10 |
| Control | 10 (paced) | 0 | −2 | 3 | 2 | 3 | 0 |

*Unpaced = minus 12 beats/min.

EXAMPLE D

Effects of Compound I and Ouabain On the Heart Contractility and Rhythmicity of the Anesthetized Dog The object of the test was to compare compound I and oubain administered alone and in combination with each other to study the inotropic effect (maximum dP/dt in the left ventricle) and a possibly arrhythmic effect. The latter included an investigation of the ability of the compounds to cause repetitive ventricular response (RVR) when the heart was electrically stimulated via an electrode on the ventricle at the electrically vulnerable phase at the end of the T-wave. Klein et al. (M. Klein, N. S. Nejad, B. Lown, F. Hagemeijer and I. Blair, Circulation Research, 29, 635 (1971)) have shown that digitalis caused RVR at a dose which was about 70% of the dose giving spontaneous ventricular arrhythmias.

The dog was anesthetized with Mebumal® 30 mg/kg bodyweight i.v. Artificial respiration was applied. The sinus-node was electrocoagulated and the heart frequency was kept constant at 180 beats/minute in each test by electrical pacing of the auricle. Mean arterial blood pressure was registered from the carotis artery. ECG was registered during the test. Further, the pressure in the left ventricle was registered via a catheter inserted through the apex and connected to a pressure transducer. The intraventricular pressure curve was derivated to obtain maximum dP/dt which is a measure of the contractile force of the heart.

The test was started with a series of control registrations, whereupon the compounds were administered 3 times by infusion during five minutes and with an interval of 50 minutes between each infusion.

In the experiment with compound I only, the compound was administered in two doses of 10 μg/kg bodyweight and then one dose of 20 μg/kg bodyweight.

ouabain corresponded to that of 20 μg/kg bodyweight of compound I. The doses of the two compound, which gave the same effect on maximum dP/dt, lowered also the enddiastolic ventricular pressure to the same degree. Compound I had no effect on the aortic blood pressure while ouabain increased this with about 10 mm Hg. This means that when the increase of maximum dP/dt was the same for the two substances, compound I had increased the ventricular contractility a little more than ouabain.

A dose of 40 μg/kg bodyweight of ouabain caused RVR in more than 50% of the experiments and a dose of 60 μg/kg bodyweight caused spontaneous arrhythmias (often a ventricular tachycardi) or RVR in all experiments. Compound I (10 and 20 μg/kg bodyweight) did not in any case cause RVR or spontaneous arrhythmia.

The combination of ouabain (20 μg/kg bodyweight) and compound I (10 or 20 μg/kg bodyweight) increased maximum dP/dt strongly and the effect corresponded to the sum of the effects of the single doses. While the combination studied increased maximum dP/dt more than 40 μg/kg bodyweight of ouabain did, the combination caused a lower frequency of RVR than said dose of ouabain did alone.

As the compound I shows a close structural relationship to other catecholamine and adrenergic agonists, which are known to cause arrhythmias a group of experiments will be described below to examine this and to compare compound I with norepinephrine. The details of this experiments and the results obtained will be given below.

Harris, A. S. Delayed Development of Ventricular Ectopic Rhythms following Coronary Occlusion, Cir. 1, p 1318, (1950) described a method of two-stage ligation of the left anterior coronary artery in the dog. This method produces a multifocal ventricular arrhythmia that generally remains persistent on the first post ligation day (day 1-24 hours post infarct). The arrhythmia slowly disappears, and by the third post-ligation day the animal has essentially a normal sinus rhythm.

Maling, H. M. and Moran, N. C., Ventricular Arrhythmias Induced by Sympathominetic Amines in Unanesthetized Dogs Following Coronary Artery Occlussion, Cir. Res. 1, p 409, (1957), have demonstrated that the injection of various catecholamines into post-myocardial infarcted dogs on day 3 to day 12 will tend to exacerbate or re-activate latent ventricular arrhythmias.

METHODS, MATERIALS AND EXPERIMENTAL DESIGN

Seventeen adult female beagle dogs were used. Their ages ranged from one to three years. These animals were divided into two groups.

The first group consisted of 12 dogs and served as a control group. All animals were subjected to a two-stage ligation of the left anterior coronary artery. On the first post operative day these twelve animals were given various experimental antiarrhythmic agents as part of a routine testing procedure. It should be noted that, due to the nature of these agents, there would be no test drug or only trace amounts of test drug in the blood on day 3, and these amounts would cause little or no change on the outcome of a third day test. It should also be noted that all twelve of these animals has at least 85% ventricular ectopic beats on the morning after surgery in order to be accepted for testing.

On the third day post infarction the dogs were suspended in a standing position in a canvas sling. No anesthesia or sedation was used. ECGs were recorded as well as blood pressure. After a control period, an infusion of 20 μg/kg min. of 1-norepinephrine was begun using a Harvard infusion/withdrawal pump. This infusion lasted 120 minutes.

The control incidence of ectopic activity was under 10%. Within a few seconds of starting the norepinephrine infusion, the rhythm became ventricular in nature and not normally conducted. This is reflected in the high incidence of ectopic activity. There was a substantially high incidence of ectopic activity for at least 90 minutes. At this time, an apparent tachyphylaxis began to occur and the rhythm became inconsistent, alternating between ectopic and normal sinus rhythm.

These experiments demonstrate the sensitivity of the infarcted dog's heart to catecholamines. The question of the effect of compound I under these conditions remained unanswered. So a series of experiments involving 5 adult female beagle dogs was designed.

These five animals were all subjected to a two stage ligation of the anterior descending coronary artery. On day 1 and day 2 each dog was suspended in a canvas sling in the standing position and ECG, blood pressure, and other physiologic measurements were taken. No test drug was administered to these animals on day 1 or day 2.

A high incidence of ectopic activity occurs on day 1 and disappears over day 2. By day 3 the incidence of ectopic activity is essentially gone. The predrug control incidence is generally below 10%.

After the control recordings were made, an intravenous infusion of compound I, 1.0 mg/kg/min, was begun. The infusion lasted twenty minutes and was then shut off. A sixty minute observation period followed. At the end of this observation period an infusion of 1-norepinephrine at 20 μg/kg/min was begun. This infusion lasted 20 minutes and was added to the experiment to establish the animal's sensitivity to this catecholamine on the third post surgical day.

The effect of compound I was not arrhythmogenic. In fact, it seems as though the few ectopic beats seen during the predrug control were slightly suppressed. This observation is based on a low incidence of predrug ectopics and may not be significant.

There was essentially no ectopic activity observed during the 60 minute postdrug observation period. The norepinephrine infusion did cause a substantial increase in ectopic activity and was also observed in the twelve control animals.

COMMENTS

These experiments demonstrate that dogs subjected to a two-stage ligation of the left anterior coronary artery develop a multi-focal ventricular arrhythmia which is very severe (85% -100% ectopic) on the first post-operative day, and degenerates after day two (to about 50% -70% ectopic). By day 3, the arrhythmia is essentially gone. By giving an infusion of 1-norepinephrine to the third post-operative day dogs, the arrhythmias may be re-activated or exaberated.

Because of the close structural relation of compound I to other adrenergic agents, concern arose as to its effect under these conditions. Therefore, similar experiments were conducted using compound I.

The results of these experiments demonstrate clearly that compound I lacks arrhythmogenic properties. At no time during the infusion of the test drug did the arrhythmia become more severe. In fact, it tended to be more of an anti-arrhythmic, since the low incidence of control ectopics seemed to be abolished during the infusion of test drug.

The results of the above-described experiments show that compounds I-IV are adrenergic beta-receptor agonists, which have a higher affinity to the beta-receptors of the heart than those of the blood vessels. The compounds I-IV have further a higher affinity to those receptors of the heart which give inotropic effects than to those which give chronotropic effects.

In the conscious dog, compound I causes a clear inotropic effect without any significant increase of the heart frequency while the inotropic effect is quite comparable to the effect of a high dose of ouabain. Compound I has a good inotropic effect when administered perorally and an acceptable duration of action.

Further, the experiments show that compound I has an evidently less arrhythmogenic effect than ouabain, when said effect is put in relation to the inotropic effects of the substances. Interaction studies with compound I and ouabain also show the interesting possibility that one can get a pronounced inotropic effect without any arrhythmogenic side effects by a combination of suitable doses of compounds I-IV and a digitalis preparation.

Studies carried out using the esters (compounds II--IV) of compound I indicate that they have about the same effect as compound I. Animal tests do not indicate any advantages of the esters above compound I. It is, however, possible that compound I may show a lower biological availability when administered perorally to human beings, because substances having free OH-groups on a phenyl nucleus very often are conjugated to a high extent when they pass the intestine-liver-passage.

Thus the esters may be advantageous to compound I, in this respect, for oral therapy.

The compounds of the present invention may be prepared in accordance with the following examples:

EXAMPLE 1

Preparation of 1-(p-benzyloxyphenoxy)-2,3-epoxypropane 25 g of p-benzyloxyphenol, 165 ml of epichlorohydrin, and 34.5 g of potassium carbonate were refluxed while stirring for 4 hours. The mixture was cooled down to room temperature and filtered, whereupon it was evaporated to dryness. The product was recrystallized from the smallest possible amount of diisopropyl ether. M.p. 68° C.

EXAMPLE 2

Preparation of 1-isopropylamino-3-(p-benzyloxyphenoxy) propanol-2 hydrochloride 25 g of 1-(p-benzyloxyphenoxy)-2,3-epoxypropane, 25 ml of isopropyl amine, and 100 ml of isopropanol were refluxed for 1,5 hours, and were then evaporated. The remaining oil was dissolved in acetone/ether (4:1) and gaseous HCl was bubbled through to pH 1 to 2. The hydrochloride thus obtained was filtered and dried. M.p. 164° C.

EXAMPLE 3

Preparation of 1-isopropylamino-3-(p-hydroxyphenoxy) propanol-2 hydrochloride 20 g of 1-(p-benzyloxyphenoxy)-3-isopropylamino-2-propanol hydrochloride were dissolved in 100 ml of 95% ethanol and were treated with active carbon (S51RL) during heating. The mixture was filtered while hot, whereupon 1.0 g of a hydrogenation catalyst (10% Pd on carbon) was added, and the mixture was hydrogenated at atmospheric pressure until the calculated amount of hydrogen was absorbed. After filtration the liquid was evaporated to dryness. The product obtained was washed with acetonitrile. M.p. 169° C.

EXAMPLE 4

Preparation of p-benzyloxyphenylisobutyrate 0.05 moles of p-benzyloxyphenol, 4.35 g of pyridine dried over potassium hydroxide, and 100 ml of dry ether were refluxed, whereupon 0.06 moles isobutyric acid chloride were added dropwise at such a rate that the reflux was under control. After the addition was complete, the total mixture was refluxed for 1 hour. In order to dissolve the pyridine hydrochloride formed, water was added. The isolated ether phase was washed twice with water and then dried over magnesium sulphate. The dried ether phase was evaporated to dryness. M.p. of final product 71° C.

EXAMPLE 5

Preparation of p-benzyloxyphenylbenzoate 0.05 moles of p-benzyloxyphenol, 4.35 g of pyridine dried over potassium hydroxide, and 100 ml of dry ether were refluxed, whereupon 0.06 moles of benzoic acid chloride were added dropwise at such a rate that the reflux was under control. After the addition had been completed, the total mixture was refluxed for 1 hour. In order to dissolve the pyridine hydrochloride formed, water was added. The isolated ether phase was washed twice with water and then dried over magnesium sulphate. The dried ether phase was evaporated to dryness. M.p. of the final product 133° C.

EXAMPLE 6

Preparation of p-benzyloxyphenylpivalate 0.05 moles of p-benzyloxyphenol, 4.35 g of pyridine dried over potassium hydroxide, and 100 ml of dry ether were refluxed, whereupon 0.06 moles of pivalic acid chloride were added dropwise at such a rate that the reflux was under control. After the addition had been completed, the total mixture was refluxed for 1 hour. In order to dissolve the pyridine hydrochloride formed, water was added. The isolated ether phase was washed twice with water and then dried over magnesium sulphate. The dried ether phase was evaporated to dryness. The melting point of the final product was 101° C.

EXAMPLE 7

Preparation of p-hydroxyphenylisobutyrate 6 g of p-benzyloxyphenylisobutyrate were hydrogenated in 95% ethanol using a Pd/C catalyst. When the calculated amount of hydrogen had been absorbed, the mixture was filtered and evaporated. The product obtained was recrystallized from ethanol. M.p. 52° C.

EXAMPLE 8

Preparation of p-hydroxyphenylbenzoate 6 g of p-benzyloxyphenylbenzoate were hydrogenated in 95% ethanol using a Pd/C-catalyst. When the calculated amount of hydrogen had been absorbed, the mixture was filtered and evaporated. The product obtained was recrystallized from ethanol. M.p. 165° C.

EXAMPLE 9

Preparation of p-hydroxyphenylpivalate 6 g of p-benzyloxyphenylpivalate were hydrogenated in 95% ethanol using a Pd/C-catalyst. When the calculated amount of hydrogen had been absorbed, the mixture was filtered and evaporated. The product obtained was recrystallized from ethanol. M.p. 101° C.

EXAMPLE 10

Preparation of p-(2,3-epoxy-1-propoxy)phenylisobutyrate 0.02 moles of p-hydroxyphenylisobutyrate from Example 7 were mixed with 26 ml of epichlorohydrin, and 5.5 g of potassium carbonate. The mixture was refluxed for 2 hours while being stirred. It was filtered and evaporated. The oil obtained was used in Example 13 below.

EXAMPLE 11

Preparation of p-(2,3-epoxy-1-propoxy)phenylbenzoate 0.02 moles of p-hydroxyphenylbenzoate from Example 8 were mixed with 26 ml of epichlorohydrin, and 5.5 g of potassium carbonate. The mixture was refluxed for 2 hours while being stirred. It was filtered and evaporated. The oil obtained was used in Example 14 below.

EXAMPLE 12

Preparation of p-(2,3-epoxy-1-propoxy)phenylpivalate 0.02 moles of p-hydroxyphenylpivalate from Example 9 were mixed with 26 ml of epichlorohydrin, and 5.5 g of potassium carbonate. The mixture was refluxed for 2 hours while being stirred. It was filtered and evaporated. The oil obtained was used in Example 15 below.

EXAMPLE 13

Preparation of the p-hydroxybenzoic acid salt of 1-isopropylamino-3-(p-isobutyryloxyphenoxy)-propanol-2

0.1 moles of the epoxide obtained in Example 10 above, 1 mole of isopropylamine, and 250 ml of isopropanol were refluxed for 1.5 hrs. The solution was evaporated and the base, p-(3-isopropylamino-2-hydroxy-1-propoxy)-phenylisobutyrate, was dissolved in ethyl acetate whereupon the p-hydroxybenzoate was precipitated using p-hydroxybenzoic acid dissolved in ethyl acetate. The salt melted at 142° C.

Example 14

Preparation of the p-hydroxybenzoic acid salt of 1-isopropylamino-3-(p-benzoyloxyphenoxy)-propanol-2

0.1 moles of the epoxide obtained in Example 11 above, 1 mole of isopropylamine, and 250 ml of isopropanol were refluxed for 1.5 hours. The solution was evaporated and the base, p-(3-isopropylamino-2-hydroxy-1-propoxy)phenylbenzoate, was dissolved in ethyl acetate whereupon its p-hydroxybenzoate was precipitated therefrom using p-hydroxybenzoic acid dissolved in ethylacetate. The salt melted at 133° C.

EXAMPLE 15

0.1 moles of the epoxide obtained in Example 12 above, 1 mole of isopropylamine, and 250 ml of isopropanol were refluxed for 1.5 hours. The solution was evaporated, and the base, p-(3--isopropylamino-2-hydroxy-1-propoxy)phenylpivalate, was dissolved in ethyl acetate, whereupon the p-hydroxybenzoate was precipitated therefrom using p-hydroxy benzoic acid dissolved in ethyl acetate. The salt melted at 163° C.

We claim:

1. The method of inducing increased inotropic effects of the human heart without inducing arrhythmogenic effects but providing an antiarrhythmogenic effect therein by administering to humans, suffering from too low heart inotropy in an amount sufficient to induce increased inotropic effects of the heart, a compound of the formula

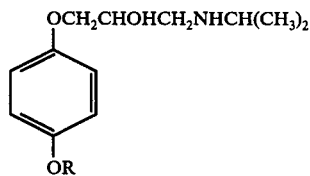

wherein R is selected from the group consisting of hydrogen or

wherein R' is selected from the group consisting of straight or branched aliphatic alkyl having 1 to 7 carbon atoms, phenyl, benzyl, and phenylethyl, wherein the phenyl nucleus may be further substituted with alkyl having 1 to 4 carbon atoms, alkoxyalkyl having 2 to 8 carbon atoms or halogen, in any position, or a therapeutically acceptable salt thereof.

2. The method according to claim 1, wherein 1-isopropylamino-3-(p-hydroxyphenoxy)-propanol-2, or a therapeutically acceptable salt thereof is administered.

3. The method according to claim 1, wherein 1-isopropylamino-3-(p-isobutyryloxyphenoxy)-propanol-2 or a therapeutically acceptable salt thereof is administered.

4. The method according to claim 1, wherein 1-isopropylamino-3-(p-benzoyloxyphenoxy)-propanol-2 or a therapeutically acceptable salt thereof is administered.

5. The method according to claim 1, wherein 1-isopropylamino-3-(p-pivaloyloxyphenoxy)-propanol-2 or a therapeutically acceptable salt thereof is administered.